US00PP21923P2

(12) United States Plant Patent
Holde

(10) Patent No.: US PP21,923 P2
(45) Date of Patent: May 17, 2011

(54) ***CAMPANULA* PLANT NAMED 'WHITE ROYAL'**

(50) Latin Name: *Campanula portenschlagiana*
Varietal Denomination: White Royal

(75) Inventor: Charlotte Holde, Odense N (DK)

(73) Assignee: Gartneriet Tvillingegaarden A/S, Odense N (DK)

( * ) Notice: Subject to any disclaimer, the term of this patent is extended or adjusted under 35 U.S.C. 154(b) by 0 days.

(21) Appl. No.: 12/653,213

(22) Filed: Dec. 9, 2009

(51) Int. Cl.
*A01H 5/00* (2006.01)

(52) U.S. Cl. ..... Plt./414

(58) Field of Classification Search ..... Plt./414
See application file for complete search history.

(56) References Cited

OTHER PUBLICATIONS

Print-out of application number and filing date from Community Plant Variety Office (CPVO) website for corresponding, CPVO application No. 2009/0727 filed Apr. 20, 2009 (2 pages). (http://www.cpvoextranet.cpvo.europa.eu).

*Primary Examiner* — Kent L Bell
(74) *Attorney, Agent, or Firm* — Foley & Lardner LLP

(57) ABSTRACT

A new distinct cultivar of *Campanula* plant named 'WHITE ROYAL' characteristics by it's upright and compact plant habit with a dense and bushy plant form; vigorous growth rate and no need for chemical growth retardation; many uniform and white flowers and dark green leaves; and good flower longevity on plant.

4 Drawing Sheets

Botanical designation: *Campanula portenschlagiana.*
Variety denomination: 'WHITE ROYAL'.

BACKGROUND OF THE INVENTION

The present invention relates to a new and distinct cultivar of *Campanula* plant, botanical known as *Campanula portenschlagiana* Schult., commonly known as Dalmatian Bellflower, and hereinafter referred to by the cultivar name 'WHITE ROYAL'.

The new *Campanula* 'WHITE ROYAL' is a product of a planned breeding program conducted by the inventor, Charlotte Holde in Odense, Denmark. The objectivity of the breeding program is to develop a new variety with a compact growth habit and white flowers.

The new *Campanula* 'WHITE ROYAL' originated from a cross made in a controlled breeding program made by the inventor in 2007 in Odense, Denmark. The female or seed parent is the unpatented, *Campanula* cultivar named '04.43.02', and the male or pollen parent is the unpatented, *Campanula* cultivar named '04.43.12'. The new *Campanula* 'WHITE ROYAL' was discovered and selected by the inventor as a compact plant with many white flowers within the progeny of the stated cross in January of 2008 in a controlled environment in Odense, Denmark.

Asexual reproduction of the new *Campanula* 'WHITE ROYAL' by vegetative cuttings used and propagated since November of 2008 in Odense, Denmark, has shown that the combination of characteristics as herein disclosed for the new cultivar are firmly fixed and retained through successive generation of asexual reproduction. The new cultivar reproduces true to type.

BRIEF SUMMARY OF THE INVENTION

The following traits have been repeatedly observed and are determined to be unique characteristics of 'WHITE ROYAL', which in combination distinguish this *Campanula* as a new and distinct cultivar:

1. upright and compact plant habit with a dense and bushy plant form;
2. vigorous growth rate and no need for chemical growth retardation;
3. many uniform and white flowers and dark green leaves; and
4. good flower longevity on plant.

Plants of the new *Campanula* 'WHITE ROYAL' differ from the plants of the parents, '04.43.02' and '04.43.12', in the following characteristics:

1. plants of 'WHITE ROYAL' have white flowers while plants of parental cultivars '04.43.02' and '04.43.12' have purple flowers;
2. plants of 'WHITE ROYAL' have darker green leaves than plants of the parental cultivar '04.43.02' and lighter green leaves than the parental cultivar '04.43.12';
3. plants of 'WHITE ROYAL' have more flowers than plants of the parental cultivars '04.43.02' and '04.43.12'; and
4. plants of 'WHITE ROYAL' are more compact than plants of the parental cultivars '04.43.02' and '04.43.12'.

The following description provides a comparison of plants of the new *Campanula* 'WHITE ROYAL' to the commercial *Campanula* cultivars 'PKMp03' (patented, U.S. Plant Pat. No. 15,826) and 'PKMP06' (patented, U.S. Plant Pat. No. 18,327). Plants of *Campanula* 'WHITE ROYAL' differ from plants of 'PKMP03' and 'PKMP06' in the following characteristics, described in Table 1:

TABLE 1

| Comparison with Comparison Varieties | | | |
|---|---|---|---|
| | | Comparison Varieties | |
| Trait | New Variety 'WHITE ROYAL' | 'PKMp03' (U.S. Plant Pat. No. 15,826) | 'PKMP06' (U.S. Plant Pat. No. 18,327) |
| Plant Diameter | About 22 cm | About 25-30 cm | About 27 cm |
| Stem Color | Green, RHS 137C | Yellow-green, RHS 144B | Green, RHS 143B |
| Immature Leaf Color (Upper Surface) | Green, RHS N137C | Yellow-green, RHS 146A | Green, RHS N138B |
| Mature Leaf Color (Upper Surface) | Green, RHS N137A | Green, RHS 137A | Green, RHS N138B |
| Venation Color (Upper Surface) | Yellow-green, RHS 146A | Green, RHS 137D | Green, RHS 138B |
| Petiole Color | Yellow-green, RHS 146A | Green, RHS 138C | Green, RHS 138B |
| Bud Color | White, between RHS 155B to 155C | White, RHS 155D, with a slight tinge of violet, RHS 85D on upper part of opening corolla | Green, RHS 143C, to white, RHS 155D |
| Flower Size: | | | |
| Diameter: | About 20 mm | About 25 mm | About 25 mm |
| Depth: | About 15 mm | About 17 mm | About 17 mm |
| Flower Fragrance | Lilac scent | None | None |
| Flower Longevity (on plant) | About 12-14 days | About 10-14 days | About 5-9 days |

BRIEF DESCRIPTION OF THE PHOTOGRAPHS

The accompanying photographs illustrate the overall appearance of the new *Campanula* 'WHITE ROYAL' showing the colors as true as is reasonably possible with colored reproductions of this type. Colors of the photographs may differ slightly from the color values cited in the detailed botanical description, which accurately describe the colors of 'WHITE ROYAL'.

DETAILED BOTANICAL DESCRIPTION

Figure 1:
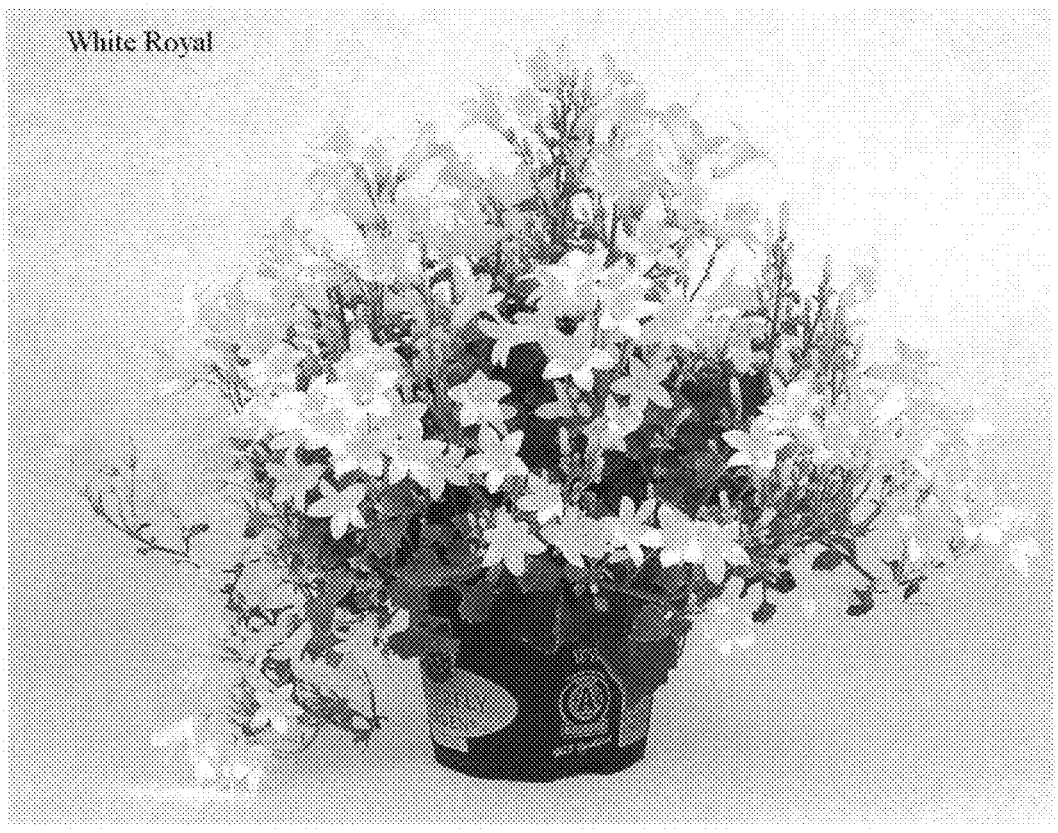
FIG. 1 shows a side perspective view of a typical flowering plant of 'WHITE ROYAL' grown in a 11 cm pot.
Figure 2:
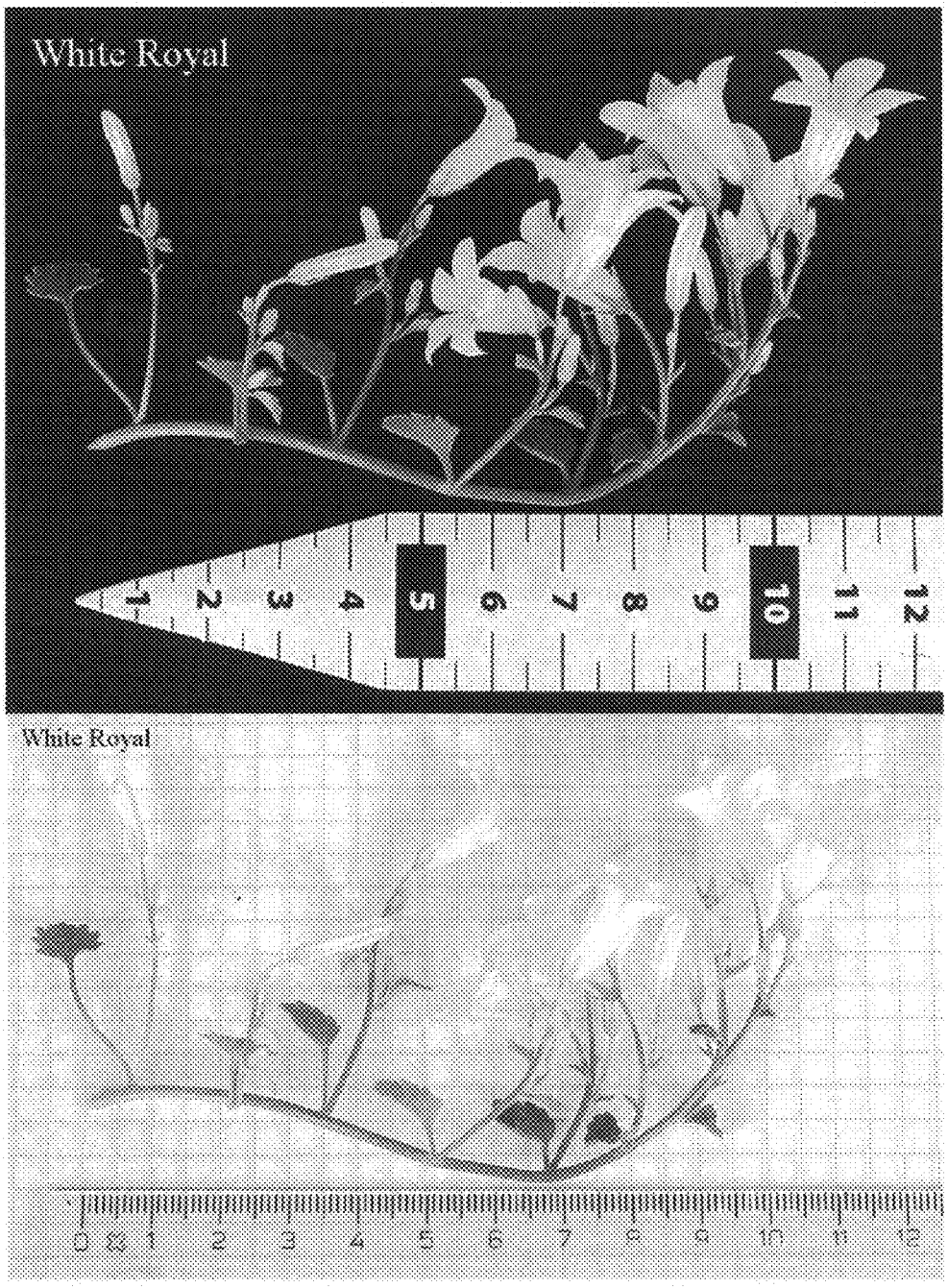
FIG. 2 shows close-up views of a typical lateral branch with leaves, buds and flowers of a raceme of 'WHITE ROYAL'.
Figure 3:
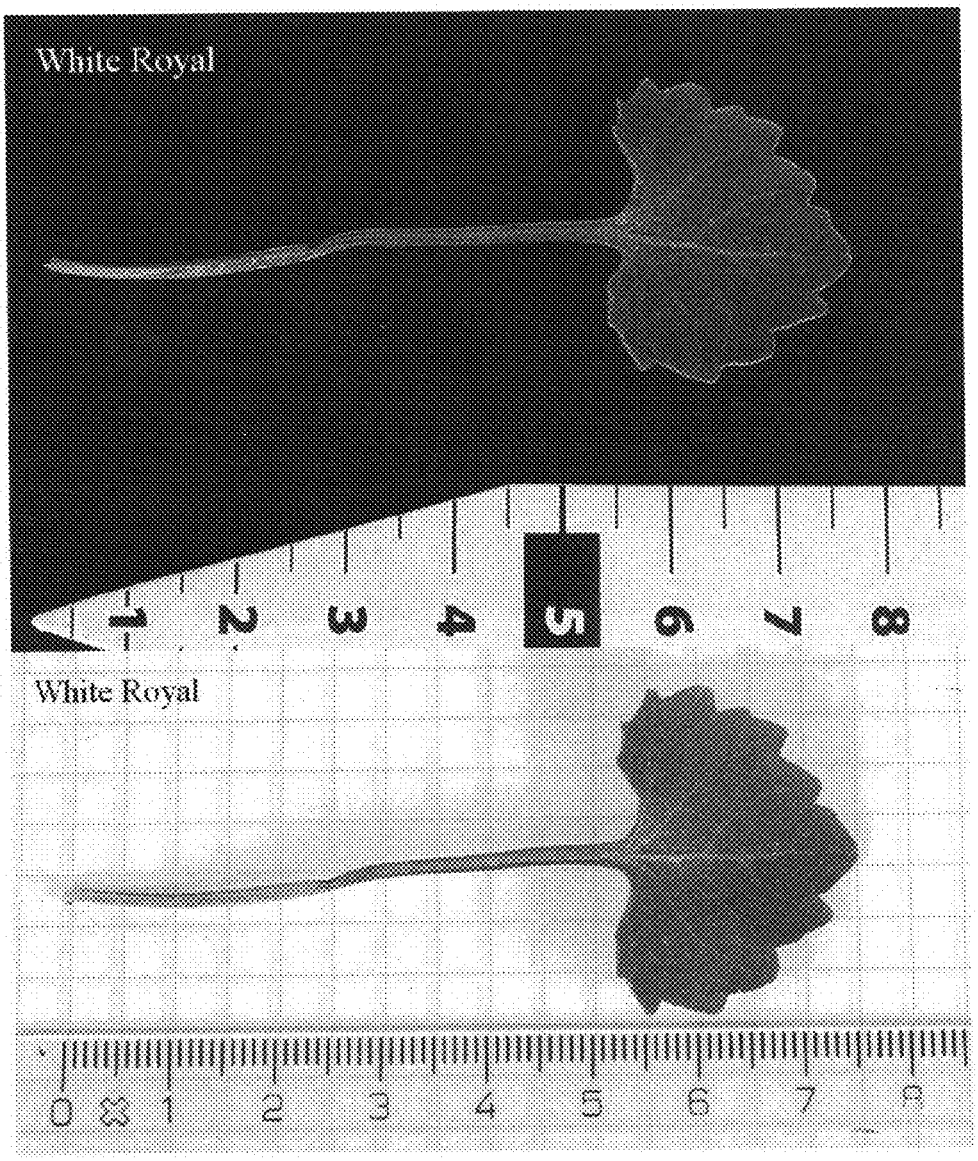
FIG. 3 shows a close-up views of a typical leaf of 'WHITE ROYAL'.
Figure 4:
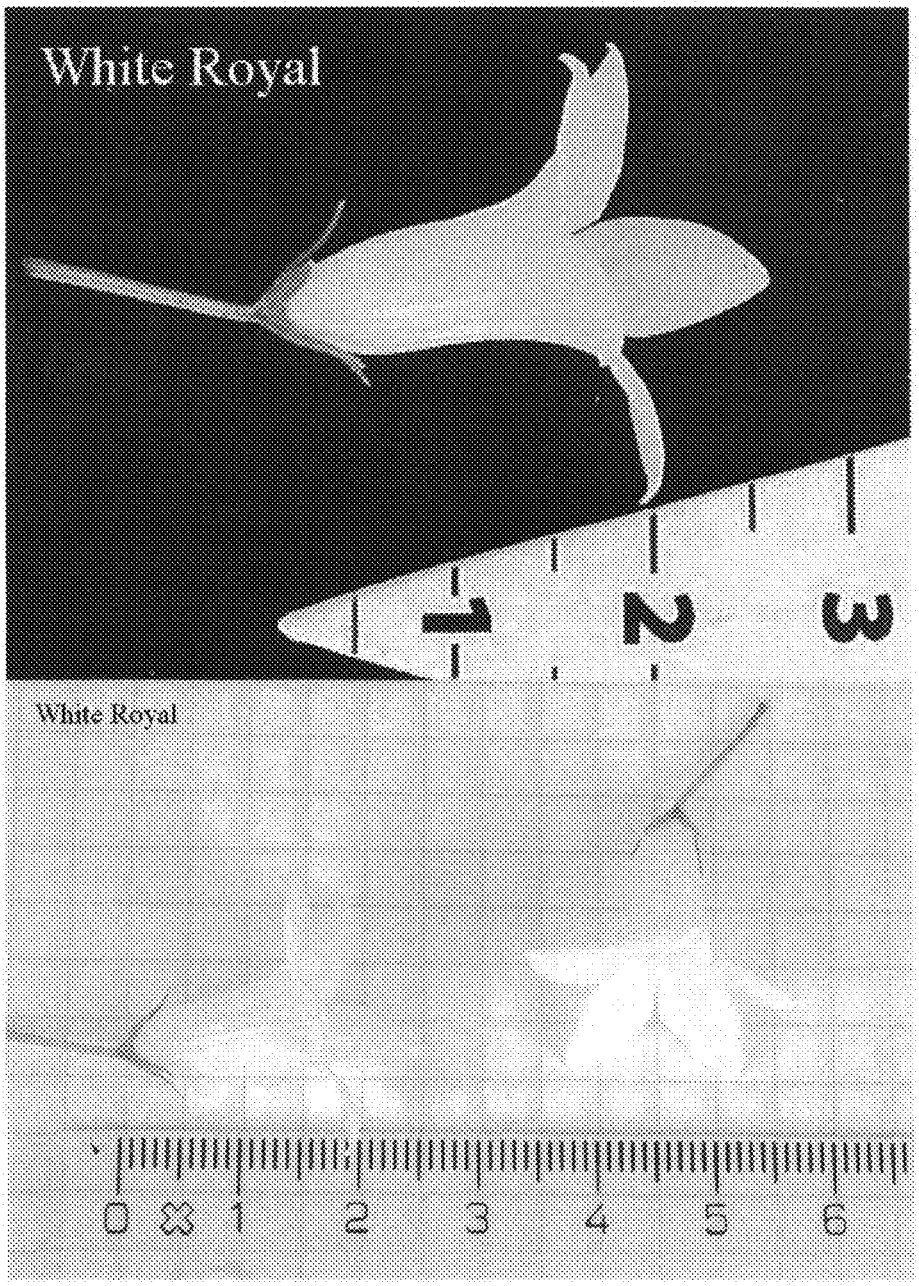
FIG. 4 shows close-up views of a typical flower of 'WHITE ROYAL'.

The new *Campanula* 'WHITE ROYAL' have not been observed under all possible environmental conditions. The phenotype of the new cultivar may vary with variations in environment such as temperature, light intensity and day length without any change in the genotype of the plant.

The aforementioned photographs, together with the following observations, measurements and values describe plants of the new *Campanula* 'WHITE ROYAL' as grown in a heated and lighted greenhouse in Odense, Denmark, under conditions which closely approximate those generally used in commercial practice. The plants of the new *Campanula* 'WHITE ROYAL' were grown in a greenhouse with an average day temperature of between 18° C. to 22° C. and an average night temperature 18 C. Ambient light levels used when growing plants of 'WHITE ROYAL' was +45 $Wm^2$. No growth retardants were used when growing plants of *Campanula* 'WHITE ROYAL'. Plants of *Campanula* 'WHITE ROYAL' are grown with 15 hour long day photoperiodic treatments from the $8^{th}$ week.

Color references are made to The Royal Horticultural Society Colour Chart (R.H.S.), $5^{th}$ Edition, 2007, except where the general colors of ordinary significance are used. The age of the plants described is about 16 to 18 weeks old after cutting, as grown in 11 cm pots.

Classification:

*Botanical.*—*Campanula portenschlagiana* Schult.

Parentage:

*Female or seed parent.*—*Campanula portenschlagiana* Schult. designated '04.43.02' (unpatented).

*Male or pollen parent.*—*Campanula portenschlagiana* Schult. designated '04.43.12' (unpatented).

Propagation:

*Type.*—Vegetative cuttings.

*Time to initiate roots.*—About 3 to 4 weeks.

*Root description.*—Fibrous, well branched.

Plant:

*Form.*—Perennial, herbaceous plant with upright plant habit and overall rounded shape. *Campanulate* flowers in racemes. Freely branching with lateral branches forming at every node; dense and bushy.

*Crop time.*—After rooting about 14 week are required to produce finished flowering plants in 11 cm pots.

*Vigor.*—Vigorous.

*Size.*—Height (soil level to top of plant plane): About 10 cm. Spread: About 22 cm.

*Stem.*—Shape: Round. Strength: Strong. Color: Green, RHS 137C.

*Lateral branches.*—Quantity: Average 60-65 per plant. Average length: (include flowers): 10 cm to 14 cm. Branch diameter: 1 m to 2 mm. Leaves per lateral branch: 5 to 7. Internode length: 10 mm to 15 mm.

Foliage:

*Type.*—Leaves single, alternate; cordate shape; broadly dentate margin; palmate venation.

*Length.*—12 mm to 25 mm.

*Width.*—20 mm to 30 mm.

*Shape.*—Cordate.

*Apex.*—Rounded to broad acuminated.

*Base.*—Cordate.

*Margin.*—Broadly dentate.

*Texture* (*both surfaces*).—Smooth, dull, glabrous.

*Pubescence.*—Short stiff hair on the abaxial side, along veins and margin.

*Color.*—Young foliage: Upper surfaces: Green, RHS N137C. Lower surfaces: Green, RHS 137B. Mature foliage: Upper surfaces: Green, RHS N137A. Lower surfaces: Yellow-green, RHS 147B.

*Venation.*—Pattern: Palmate.

*Color.*—Upper surface: Yellow-green, RHS 146A. Lower surface: Yellow-green, RHS 146A to RHS 146B.

*Petiole.*—Length: 3 cm to 7 cm. Diameter: 1 mm to 2 mm. Texture: Smooth with short stiff hair. Color: Yellow-green, RHS 146A.

Flower:

*Flower arrangement and shape.*—Single upright flowers in racemes. *Campanulate* flowers with small star shaped calyx.

*Natural flowering season.*—Continuous throughout the spring and summer. Season can be extended by long day treatments.

*Flower longevity on the plant.*—About 12 to 14 days; however, longevity of individual flowers is highly dependent on temperature and light conditions. Flowers persistent.

*Fragrance.*—Lilac scent.

*Inflorescence size.*—Length/height: About 8 cm to 10 cm. Diameter: 50 mm.

*Number of flowers per inflorescence.*—About 4-6.

*Number of flowers and buds per plant.*—About 1500.

*Flowers.*—Depth: About 15 mm. Diameter: About 20 mm. Acute petal lobes: 7-9 mm long and 5-6 mm wide. Corolla color: Upper surfaces: White, NN155C. Lower surface: White, NN155C.

*Buds.*—Length: Up to 15 mm. Diameter: Up to 3 mm. Shape: Oblong, ridged. Color: White, RHS 155B to RHS 155C.

*Petals.*—Arrangement: Single, sympetalous. Quantity per flower: 5. Overall shape: Bell-shaped, campanulate. Apex shape: Acute. Base shape: Fused. Length: 7 mm to 9 mm. Width: 5 mm to 6 mm. Margin: Entire. Texture: Velvety. Color (when opening): Upper surfaces: White, RHS NN155C. Lower surfaces: White, RHS NN155C.

*Color* (*when opened*).—Upper surfaces: White, RHS NN155C. Lower surfaces: White, RHS NN155C.

*Fading.*—None.

*Sepals.*—Arrangement: Free arrangement. Quantity per flower: 5. Overall shape: Arrow-shaped. Apex: Cuspidate. Base: Fused. Length: 5 mm. Width: 1 mm. Margin: Entire. Texture: Dull, with short stiff hair on abaxial side and margin. Color: Immature (both surfaces): Yellow-green, RHS 144B. Mature (both surfaces): Green, RHS 143A.

*Peduncle.*—Strength: Moderately strong. Length: About 20 mm to 25 mm. Diameter: 1 mm. Color: Green, RHS 143A.

Reproductive organs:

*Androecium.*—Stamen: Quantity per flower: 5, fused until pollen is shed. Anther: Shape: Fused. Diameter: About 1 mm. Color: Yellow-white, RHS 158B. Pollen: Amount: Average production. Color: Yellow-white, RHS 158B.

*Gynoecium.*—Pistil: Quantity per flower: 1. Length: About 12 mm. Stigma: Shape: Tripartite. Color: White, RHS 155B. Style: Length: About 11 mm. Color: White, RHS 155C. Ovary: Color: Yellow-green, 154B.

Seed: None observed.

Disease/pest resistance: Not observed.

Disease/pest susceptibility: Not observed.

What claimed is:

1. A new and distinct cultivar of *Campanula* plant named 'WHITE ROYAL', as described and illustrated herein.

* * * * *

UNITED STATES PATENT AND TRADEMARK OFFICE

CERTIFICATE OF CORRECTION

PATENT NO. : PP21,923 P2
APPLICATION NO. : 12/653213
DATED : May 17, 2011
INVENTOR(S) : Charlotte Holde It is certified that error appears in the above-identified patent and that said Letters Patent is hereby corrected as shown below:

IN THE SPECIFICATION:

On page 2, column 3, in Table 1 at about line 11, the Stem Color of New Variety 'WHITE ROYAL' should be --Green, RHS 137B--.

On page 2, column 4, line 35, "RHS 137C" should be --RHS 137B--.

Signed and Sealed this
Nineteenth Day of July, 2011

David J. Kappos

David J. Kappos
*Director of the United States Patent and Trademark Office*